United States Patent
Almansour et al.

(10) Patent No.: US 9,873,699 B1
(45) Date of Patent: *Jan. 23, 2018

(54) ANTI-CANCER AGENTS

(71) Applicant: KING SAUD UNIVERSITY, Riyadh (SA)

(72) Inventors: Abdulrahman I. Almansour, Riyadh (SA); Natarajan Arumugam, Riyadh (SA); Raju Suresh Kumar, Riyadh (SA); Periasamy Vaiyapuri Subbarayan, Riyadh (SA); Ali Abdullah Alshatwi, Riyadh (SA); Jegan Athinarayanan, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/462,744

(22) Filed: Mar. 17, 2017

(51) Int. Cl.
  *C07D 471/20* (2006.01)
(52) U.S. Cl.
  CPC .................. *C07D 471/20* (2013.01)
(58) Field of Classification Search
  CPC .................................. C07D 471/20
  USPC ....................................... 514/278
  See application file for complete search history.

(56) References Cited

U.S. PATENT DOCUMENTS 6,358,507 B1    3/2002   Fokas et al.
9,486,444 B1 *  11/2016  Almansour .......... A61K 31/435

OTHER PUBLICATIONS

Xiao-Fang Li et al, 2003, 1"-Benzyl-5"-benzylidene-1'-methyl-4'-phenykl-1H-indole-3-spiro-2'-pyrrolidine-3'-spiro-3"-piperidine-2(3H),3"-dione.*

Almansour et al . "Facile, Regio- and Diastereoselective Synthesis of Spiro-Pyrrolidine and Pyrrlizine Derivatives and Evaluation of Their Antiproliferative Activities," Mol., Jul. 10, 2014, 19, pp. 10033-10055.*

Rani et al., "One-Pot Access to a Library of Dispiro Oxindole-pyrrolidine/pyrrolothiazole-thiochromane Hybrids via Three-Component 1,3-Dipolar Cycloaddition Reactions." ACS Comb, Sci., Apr. 13, 2016, 18 (6), pp. 337-342.

Almansour et al., "Facile, Regio- and Diastereoselective Synthesis of Spiro-Pyrrolidine and Pyrrlizine Derivatives and Evaluation of Their Antiproliferative Activities," Mol., Jul. 10, 2014, 19, pp. 10033-10055.

Arun et al., "Novel Spirooxindole-pyrrolidine Compounds: Synthesis, Anticancer and Molecular Docking Studies," Eur. J. Med. Chem., Jan. 3, 2014, 74 (3), pp. 50-64.

* cited by examiner

*Primary Examiner* — Rita J Desai
(74) *Attorney, Agent, or Firm* — Richard C. Litman

(57) ABSTRACT

An anti-cancer agent having the formula:

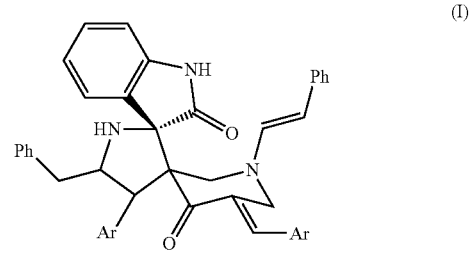

wherein Ph is a phenyl group and Ar is an aromatic group independently selected from the group consisting of phenyl, 2-bromophenyl, 4-bromophenyl, 2-chlorophenyl, 2,4, dichlorophenyl, 4-chlorophenyl, 2-methylphenyl, 3-methylphenyl, 4-methylphenyl, 2 methoxyphenyl, 3-methoxyphenyl, 4-methoxyphenyl, and 3-nitrophenyl; or a pharmaceutically acceptable salt thereof.

9 Claims, 6 Drawing Sheets

ANTI-CANCER AGENTS

BACKGROUND OF THE INVENTION

1. Field of the Invention

The present invention relates to organic heterocyclics and particularly to the synthesis of dispiropyrrolidine tethered piperidone compounds as anti-cancer agents.

2. Description of the Related Art

Cancer is among the world's leading causes of death. According to the latest figures of the International Agency for Research on Cancer (IARC) the global cancer burden rose to 14.1 million new cases and 8.2 million cancer deaths in 2012. It is estimated that there will be 19.3 million new cancer cases per year by 2025 due to the growth of the aging population. Despite recent advances in cancer biology and the development of anti-cancer agents, treatments can be ineffective and patients frequently relapse, particularly for brain, pancreas, and late stage lung cancers.

Currently, many anti-cancer drugs have been approved by FDA, viz., Fluorouracil, Bevacizumab, Irinotecan Hydrochloride, Anastrozole, Pamidronate Disodium, Exemestane, Capecitabine, Cyclophosphamide, Docetaxel, Doxorubicin Hydrochloride, Epirubicin Hydrochloride, Eribulin Mesylate, Everolimus, Exemestane, Tamoxifen Citrate, Paclitaxel, Vinblastine sulfate and bleomycin, etc. These are mainline drugs (MLD) and are categorized according to their mechanism of action, such as alkylating agents (platinum drugs-oxaliplatin), anti-metabolites (5-fluorouracil), mitotic inhibitors (vinca alkaloids-Vinblastine sulfate), topoisomerase inhibitors (doxorubicin), Cytotoxic antibiotics (bleomycin), etc. Alkylating agents (including platinum based drugs) bind covalently to DNA strands, subsequently disturbing cell division and ending up with programmed cell death (PCD). Antimetabolites are structurally similar to nucleotides that inhibit the enzymes involved in DNA and RNA synthesis and end up disincorporating cell replication machinery. Vinca alkaloids are anti-microtubule agents that prevent microtubule formation in dividing cells and subsequently incomplete mitosis. Topoisomerase inhibitors (e.g. doxorubicin) inhibit the topoisomerase enzymes, which are mainly involved in DNA double helix unwinding. Improper replication or transcription by doxorubicin leads to PCD. Cytotoxic antibiotics (bleomycin) trigger redox-mediated DNA damage and cause PCD. Hence, most of these currently practicing MLDs function as apoptotic inducers by triggering specific pathways to cause tumor/cancer cell death.

Apoptosis, autophagy and necro-apoptosis are different kinds of PCD. More than 20 different pathways contribute to different modes of cell death in tumor cells. In the pathway towards the induction of cancer, evading specific PCD (i.e., apoptosis) is one of the fundamental mechanisms. The direct molecular link between cancer pathogenesis and dysregulation of PCD are interlinked mechanisms that can be used as therapeutic targets by triggering PCD mechanisms (induced apoptosis) in tumor/cancer cells. Therefore, screening by induction of apoptosis has potential application in target-based cancer therapy, one of the desired endpoints in cancer therapy.

Thus, dispiropyrrolidine tethered piperidones as anti-cancer agents solving the aforementioned problems is desired.

SUMMARY OF THE INVENTION

The anti-cancer agents include dispiropyrrolidine tethered piperidone having the formula:

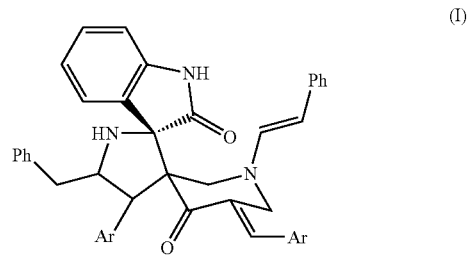

(I)

wherein Ph is a phenyl group and Ar is phenyl, 2-bromophenyl, 4-bromophenyl, 2-chlorophenyl, 2,4 dichlorophenyl, 4-chlorophenyl, 2-methylphenyl, 3-methylphenyl, 4 methylphenyl, 2-methoxyphenyl, 3-methoxyphenyl, 4-methoxyphenyl, or 3-nitrophenyl; or a pharmaceutically acceptable salt thereof.

A method of making dispiropyrrolidine tethered piperidone compound of formula (I) includes the step of reacting indoline-2,3-dione and L-phenylalanine with (3E,5E)-3,5-bis(4-arylbenzylidene)piperidin-4-one in an organic solvent forming a reaction mixture thereby yielding the dispiropyrrolidine tethered piperidone compound of formula (I).

An effective amount of the dispiropyrrolidine tethered piperidone compound of formula (I) may be administered to a cancer patient in need thereof for inhibiting proliferation of cancer cells.

These and other features of the present invention will become readily apparent upon further review of the following specification

BRIEF DESCRIPTION OF THE DRAWINGS

FIG. 3 shows the selected proton ($^1$H) and carbon-13 ($^{13}$C) NMR chemical shifts of compound 4a.

Similar reference characters denote corresponding features consistently throughout the attached drawings.

DETAILED DESCRIPTION OF THE PREFERRED EMBODIMENTS

Figure 1:
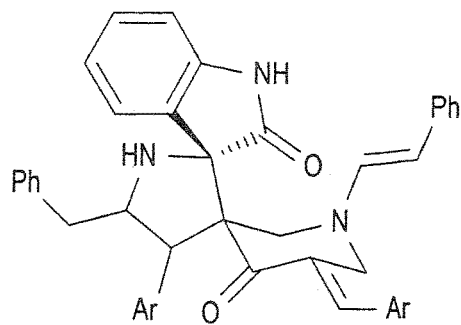
FIG. 1 shows the structural formula of the compound of formula (I).

The dispiropyrrolidine-tethered piperidone compounds include compounds having the general formula:

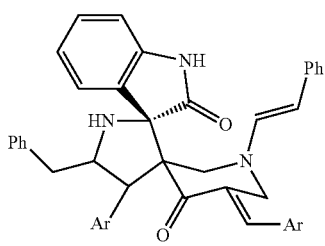

wherein Ph is a phenyl group and Ar is an aromatic group independently selected from the group consisting of phenyl, 2-bromophenyl, 4-bromophenyl, 2-chlorophenyl, 2,4, dichlorophenyl, 4-chlorophenyl, 2-methylphenyl, 3-methylphenyl, 4-methylphenyl, 2-methoxyphenyl, 3-methoxyphenyl, 4-methoxyphenyl, and 3-nitrophenyl; or a pharmaceutically acceptable salt thereof. The compound of Formula I can be formulated into a composition including a pharmaceutically acceptable carrier, excipient or diluent.

Apoptosis induction is one of the most important ways by which the anti-cancer agents successfully activate a programmed cancer cell death. The anti-cancer properties of the anti-cancer agents (Forumula I compounds) have been assessed on FaDu hypopharyngeal tumor cells, as described herein, by cell viability and fluorescent microscopic assay. It is believed that the compounds arrest cancer cell growth by increasing the percentage of early apoptotic and late apoptotic cells. The results obtained by the present inventors provide strong evidence that the anti-cancer agents induce nuclear fragmentation and morphological changes via apoptosis dose dependently in FaDu hypopharyngeal tumor cells. Accordingly, the anti-cancer agents can be used for cancer therapeutics.

Spiropyrrolidine-oxindole scaffolds are prevalent in several natural alkaloids such as coerulescine IV, horsfiline V, elacomine VI, alstonisine VII, mitraphylline VIII and possesses many biological activities including potent antitumor properties against human cancer cell lines, neuroblastoma SKN-BE and malignant glioma GAMG. Among these, natural spirooxindoles like Spirotryprostatins A and B also show excellent anticancer activities. Specifically, the synthesized spirooxindoles such as MI-888 have been in preclinical research for the treatment of human cancers. Piperidinone is another important heterocyclic scaffold that is of great interest in the pharmaceutical industry as its derivatives are a novel cluster of tumor specific cytotoxins and display excellent growth inhibiting and apoptotic inducing properties against a number of human cancer cell lines. And, these derivatives are especially effective against colon cancers and leukemic cells, and have been reported to be more potent cytotoxins than 5-fluorouracil and melphalan. In addition, piperidinone derivatives selectively inhibits coactivator-associated arginine methyltransferase 1 (CARM1), a valuable target for hormone-dependent tumors such as prostate and breast cancers. Bisarylidenepiperidin-4-ones were used as dipolarophilic components in many cycloaddition reactions to obtain spiroheterocyclic hybrids comprising piperidin-4-one, pyrrolidine and other heterocyclic units. Previously, the present inventors synthesized spiroheterocyclic hybrids including piperidin-4-one unit through multicomponent 1,3-diplar cycloaddition and/or domino reaction sequence.

Figure 2:
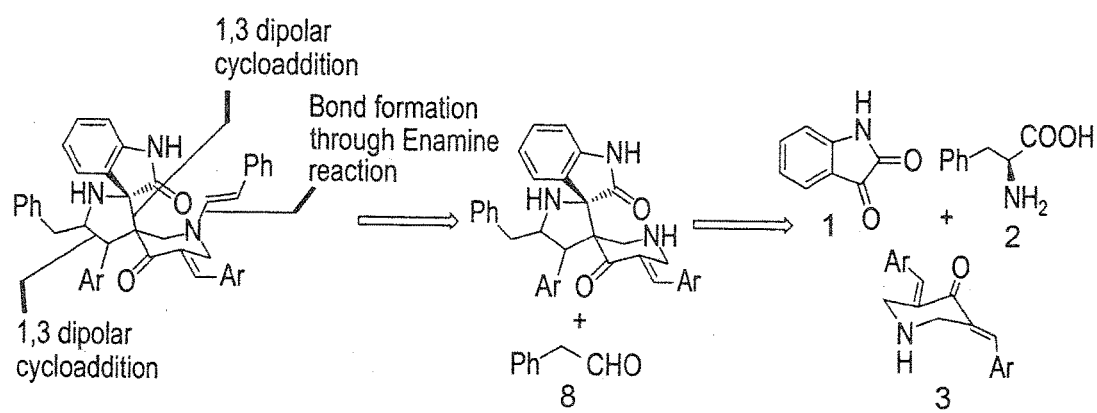
FIG. 2 shows the retrosynthetic pathway of the formation of dispiropyrrolidine tethered piperidone of formula (I).

Building on their previous studies on 1,3-dipolar cycloaddition reactions, the present inventors have synthesized spiropyrrolidine-oxindole frameworks comprising arylidenepiperidin-4-one substructures through a domino three-component dipolar cyloaddition reaction, in order to screen the resulting library for in vitro anticancer activity. The domino sequence reaction is provided in FIG. 2.

A method for treating cancer can include the step of administering to a patient in need thereof an effective amount of a compound of Formula I for inhibiting the proliferation of cancer cells. The effective amount can include a dose amount of the compound of Formula I that provides an in vivo concentration of about 10 μm to about 100 μm. As would be understood by those skilled in the art of treating cancer, the term "treatment" does not necessarily mean that the cancer is completely cured. The term "treatment" encompasses any inhibition of the proliferation of the cancer cells. As understood by those skilled in the art, the half maximal inhibitory concentration ($IC_{50}$) is a measure of the effectiveness of a substance in inhibiting a specific biological or biochemical function.

A pharmaceutically acceptable salt includes any non-toxic salt of the present anti-cancer agents, which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methyinitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

The anti-cancer agents can be administered to a patient in need thereof. For example, the anti-cancer agents can be used to treat a patient suffering from cancer. The cancer can include colon cancer, breast cancer, prostate cancer, and/or blood cancer.

The anti-cancer agents can be administered by any conventional route of administration, including, but not limited to, intravenous, oral, subcutaneous, intramuscular, intradermal and parenteral. Depending on the route of administration, the anti-cancer agents can be constituted into any form. For example, forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

Also provided is a pharmaceutical composition including an anti-cancer agent. To prepare the pharmaceutical composition, one or more anti-cancer agents or salt thereof, as the active ingredient, is intimately admixed with a pharmaceutical carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

The anti-cancer agents or dispiropyrrolidine tethered piperidone compounds of Formula I, can be synthesized by providing a reaction mixture including indoline-2,3-dione, L-phenylalanine, and N-arylidene piperidone starting precursor, e.g., (3E,5E)-3,5-bis(4-arylbenzylidene)piperidin-4-one. The reaction mixture can be refluxed in an organic solvent to yield the dispiropyrrolidine tethered piperidone compound of Formula I or anti-cancer agents. In this reaction, a molar ratio of indoline-2,3-dione:L-phenylalanine:N-arylidene piperidone is typically chosen to be about 2:2:1. After completion of the reaction, the reaction mixture can be cooled and the precipitate can be recovered by filtering. The recovered precipitate can be washed with ethyl acetate and dried under pressure. An exemplary anti-cancer agent of Formula I is 5'-benzyl-5-spiro[3,2']oxindolopyrrolidino-4'-(methylphenyl)-1"-styryl-5-benzylidene-spiro[3'.3"]piperidi-4"-one (4a). The crude products can then be purified in cold methanol at room temperature.

The present teachings will be understood more readily by reference to the following examples, which are provided by way of illustration.

Example 1

Synthesis of N-Arylidene Piperidone Tethered Dispiropyrrolidine (Compounds 4a-m)

A solution of indoline-2,3-dione (2.72 mmol), L-phenylalanine (2.72 mmol) and (3E,5E)-3,5-bis(4-arylbenzylidene)piperidin-4-one (1.36 mmol) was refluxed in methanol for 2 hours. After completion of the reaction as evidenced from thin layer chromatography (TLC), the reaction mixture was cooled to room temperature; a white solid slowly precipitated out in the bottom of the flask. The excess methanol was decanted and the crude product was washed with cold ethylacetate (2 ml×5). The product, e.g., one of compounds 4a-m depending upon the N-arylidene piperidone starting precursor used, was dried under reduced pressure.

The product was purified in cold methanol at room temperature, e.g., the compound (100 mg) was washed with cold methanol (10 ml×3), and dried at room temperature to afford a colorless solid.

5'-benzyl-5-spiro[3,2']oxindolopyrrolidino-4'-(methylphenyl)-1"-styryl-5-benzylidene-spiro[3'.3"]piperidi-4"-one (4a): Colorless crystals, 90%. The $^1$H NMR (CDCl$_3$, 400 MHz) dat is as follows: δ/ppm 4.95 (d, J=14.92 Hz, 1H), 4.75-4.78 (m, 1H), 4.38 (d, J=10.28 Hz, 1H), 3.81 (d, J=13.92 Hz, 1H), 3.66 (d, J=16.16 Hz, 1H), 3.34 (d, J=15.40 Hz, 1H), 3.03-3.07 (m, 1H), 2.79-2.82 (m, 1H), 2.57 (d, J=13.20 Hz, 1H), 6.61-6.64 (m, 2H), 6.89-7.48 (m, 24H, Ar), 7.68 (s, 1H, NH); $^{13}$C NMR (CDCl$_3$, 100 MHz): δC/ppm 39.48, 46.93, 53.01, 53.51, 61.24, 66.96, 71.09, 100.03, 109.26, 122.30, 124.09, 124.18, 126.37, 126.69, 127.23, 127.85, 128.46, 128.62, 128.64, 128.72, 129.27, 129.35, 130.30, 130.69, 134.62, 137.26, 138.53, 138.64, 138.78, 139.15, 141.01, 179.18, 197.79. EI-MS: m/z 627 (M$^+$). Anal. Calcd for C$_{43}$H$_{37}$N$_3$O$_2$: C, 82.27; H, 5.94; N, 6.69. Found: C, 82.39; H, 5.81; N, 6.57.

5'-benzyl-4'-(2-bromopheynyl)-5-spiro[3,2']oxindolopyrrolidino-4'-(2-bromophenyl-1"-styryl-5-benzylidene-spiro[3'.3"]piperidi-4"-one (4b): Colorless crystals, 92%; $^1$H NMR (CDCl$_3$, 400 MHz): δ/ppm 4.88-4.91 (m, 1H), 4.57-4.62 (m, 2H), 3.58 (d, J=16.16 Hz, 1H), 3.21 (d, J=13.92 Hz, 1H), 3.00-3.08 (m, 1H), 2.97-2.99 (m, 1H), 2.74 (d, J=15.4 Hz, 1H), 6.35 (d, J=13.92 Hz, 1H), 6.65 (d, J=8.04, 1H), 6.92-7.69 (m, 22H, Ar), 7.95 (s, 1H, NH); $^{13}$C NMR (CDCl$_3$, 100 MHz): δ/ppm 39.58, 46.92, 53.24, 53.57, 61.29, 65.45, 73.57, 100.13, 109.16, 122.39, 123.75, 125.18, 126.14, 126.74, 127.28, 127.89, 128.30, 128.40, 129.26, 129.34, 129.41, 129.44, 130.38, 130.78, 130.86, 132.82, 132.83, 135.07, 135.35, 136. 137.35, 138.59, 138.69, 138.81, 139.21 141.17, 179.24, 197.81. EI-MS: m/z 785 (M$^+$). Anal. Calcd for C$_{43}$H$_{35}$Br$_2$N$_3$O$_2$: C, 65.74; H, 4.49; N, 5.35; Found: C, 65.86; H, 4.61; N, 5.47.

5'-benzyl-4'-(4-bromopheynyl)-5-spiro[3,2']oxindolopyrrolidino-4'-(4-bromophenyl-1"-styryl-5-benzylidene-spiro[3'.3"]piperidi-4"-one (4c): Colorless crystals, 91%; $^1$H NMR (CDCl$_3$, 400 MHz): δ/ppm 4.94 (d, J=13.92 Hz, 1H), 4.66-4.70 (m, 1H), 4.30 (d, J=10.24 Hz, 1H), 3.74 (d, J=13.96 Hz, 1H), 3.65 (d, J=15.4 Hz, 1H), 3.27 (d, J=15.76 Hz, 1H), 2.98-3.03 (dd, J=13.92, 2.96 Hz, 1H), 2.77-2.82 (m, J=13.92, 8.08 Hz, 1H), 2.56 (d, J=13.2 Hz, 1H), 6.59-6.64 (m, 2H), 6.89-7.49 (m, 22H, Ar); $^{13}$C NMR (CDCl$_3$, 100 MHz): δ/ppm 39.52, 46.96, 52.94, 53.06, 61.53, 66.73, 71.15, 100.58, 109.38, 122.31, 124.40, 126.48, 127.56, 128.24, 128.24, 128.50, 128.64, 129.28, 129.41, 131.13, 131.62, 131.84, 131.95, 133.35, 136.30, 137.91, 138.21, 138.29, 138.48, 141.01, 179.22, 197.94. EI-MS: m/z 785 (M$^+$). Anal. Calcd for C$_{43}$H$_{35}$Br$_2$N$_3$O$_2$: C, 65.74; H, 4.49; N, 5.35; Found: C, 65.86; H, 4.62; N, 5.47.

5'-benzyl-4'-(2-chloropheynyl)-5-spiro[3,2']oxindolopyrrolidino-4'-(2-chlorophenyl-1"-styryl-5-benzylidene-spiro[3'.3"]piperidi-4"-one (4d): Colorless crystals, 89%; $^1$H NMR (CDCl$_3$, 400 MHz): δ/ppm 4.88-4.92 (m, 1H), 4.62-4.65 (m, 2H), 3.59 (d, J=16.16 Hz, 1H), 3.26 (d, J=13.92 Hz, 1H), 2.96-3.10 (m, 2H), 2.77-2.86 (m, 2H), 6.38 (d, J=13.92 Hz, 1H), 6.64 (d, J=7.32 Hz, 1H), 6.89-7.42 (m, 22H, Ar), 7.76 (s, 1H); $^{13}$C NMR (CDCl$_3$, 100 MHz): δ/ppm 40.53, 46.15, 51.89, 52.62, 62.90, 65.46, 73.28, 98.25, 109.78, 122.55, 123.84, 126.25, 127.52, 127.69, 128.09, 128.61, 129.18, 129.29, 130.03, 130.36, 130.50, 132.94, 133.11, 135.07, 135.80, 135.92, 136.20, 137.94, 138.51, 139.08, 141.16, 177.48, 200.01. EI-MS: m/z 696 (M$^+$). Anal. Calcd for C$_{43}$H$_{35}$Cl$_2$N$_3$O$_2$: C, 74.13; H, 5.06; N, 6.03; Found: C, 74.24; H, 5.17; N, 6.15.

5'-benzyl-4'-(2,4-dichloropheynyl)-5-spiro[3,2']oxindolopyrrolidino-4'-(2,4-dichlorophenyl-1"-styryl-5-benzylidene-spiro[3'.3"]piperidi-4"-one (4e): Colorless crystals, 90%; $^1$H NMR (CDCl$_3$, 400 MHz): δ/ppm 4.82-4.87 (m, 1H), 4.58-4.67 (m, 2H), 3.55-60 (d, J=16.16 Hz, 1H), 3.23 (d, J=13.92, 1H), 2.96-3.01 (m, 1H), 2.77-2.81 (m, 2H), 6.33 (d, J=13.92 Hz, 1H), 6.66 (d, J=7.36 Hz, 1H), 6.90-7.50 (m, 20H, Ar), 7.58 (s, 1H, NH); $^{13}$C NMR (CDCl$_3$, 100 MHz): δ/ppm 39.54, 46.92, 53.17, 53.65, 61.36, 67.01, 71.18, 100.12, 109.30, 122.31, 124.18, 124.20, 126.40, 126.70, 127.29, 127.91, 128.49, 128.77, 128.69, 128.65, 129.29, 129.35, 130.37, 130.71, 134.69, 137.29, 138.55, 138.69, 138.86, 139.24, 141.11, 179.26, 197.64. EI-MS: m/z 765 (M+). Anal. Calcd for C$_{43}$H$_{33}$Cl$_4$N$_3$O$_2$: C, 67.46; H, 4.34; N, 5.49. Found: C, 67.58; H, 4.47; N, 5.62.

5'-benzyl-4'-(4-chloropheynyl)-5-spiro[3,2']oxindolopyrrolidino-4'-(4-chlorophenyl-1"-styryl-5-benzylidene-spiro[3'.3"]piperidi-4"-one (4f): Colorless crystals, 92%; $^1$H NMR (CDCl$_3$, 400 MHz): δ/ppm 4.94 (d, J=13.96 Hz, 1H), 4.67-4.68 (m, 1H), 4.32 (d, J=10.4 Hz, 1H), 3.75 (d, J=13.16

Hz, 1H), 3.62 (d, J=16.12 Hz, 1H), 3.29 (d, J=16.16 Hz, 1H), 2.97-3.00 (m, 1H), 2.77-2.8 (m, 1H), 2.55 (d, J=13.92 Hz, 1H), 6.56-6.64 (m, 2H), 6.88-7.39 (m, 22H, Ar), 7.80 (s, 1H, NH); $^{13}$C NMR (CDCl$_3$, 100 MHz): δ/ppm 39.55, 46.98, 52.88, 52.94, 61.47, 66.73, 71.12, 100.55, 109.40, 122.29, 124.14, 124.37, 126.47, 126.63, 127.68, 128.47, 128.62, 128.87, 128.99, 129.33, 129.38, 131.05, 131.46, 132.95, 133.10, 135.57, 135.80, 137.83, 138.21, 138.32, 138.51, 141.07, 179.24, 197.50. EI-MS: m/z 696 (M$^+$). Anal. Calcd for $C_{43}H_{35}Cl_2N_3O_2$: C, 74.13; H, 5.06; N, 6.03 Found: C, 74.24; H, 5.18; N, 6.15.

5'-benzyl-4'-(2-tolyl)-5-spiro[3,2']oxindolopyrrolidino-4'-(2-methylphenyl)-1"-styryl-5-benzylidene-spiro[3'.3"]piperidi-4"-one (4g): Colorless crystals, 88%; $^1$H NMR (CDCl$_3$, 400 MHz): δ/ppm 4.91-4.93 (m, 1H), 4.70 (d, J=13.92 Hz, 1H), 4.49 (d, J=10.28 Hz, 1H), 3.53-3.59 (m, 2H), 2.97-3.09 (m, 1H), 2.83-2.89 (m, 2H), 2.63 (d, J=13.96 Hz, 1H), 2.23 (s, 3H), 2.21 (s, 3H), 6.48 (d, J=14.64 hz, 1H), 6.65 (d, J=7.32 Hz 1H), 6.76 (d, J=8.08 Hz, 1H), 6.92-7.76 (m, 21H, Ar), 7.65 (s, 1H, NH); $^{13}$C NMR (CDCl$_3$, 100 MHz): δ/ppm 20.06, 20.99, 40.12, 46.22, 50.46, 53.21, 63.16, 65.67, 72.53, 98.54, 109.58, 123.87, 125.75, 126.30, 126.51, 126.87, 128.43, 128.60, 129.15, 129.29, 130.41, 131.54, 133.67, 136.04, 137.86, 138.01, 138.24, 138.43, 138.95, 139.08, 141.22, 177.91, 199.89. EI-MS: m/z 655 (M+). Anal. Calcd for $C_{45}H_{41}N_3O_2$; C, 82.41; H, 6.30; N, 6.41; Found: C, 82.54; H, 6.42; N, 6.53.

5'-benzyl-4'-(3-tolyl)-5-spiro[3,2']oxindolopyrrolidino-4'-(3-methylphenyl)-1"-styryl-5-benzylidene-spiro[3'.3"]piperidi-4"-one (4h): Colorless crystals, 86%; $^1$H NMR (CDCl$_3$, 400 MHz): δ/ppm 4.95 (d, J=13.96 Hz, 1H), 4.72-4.76 (m, 1H), 4.34 (d, J=11.0 Hz, 1H), 3.82 (d, J=13.92 Hz, 1H), 3.66 (d, J=17.6 Hz, 1H), 3.36 (d, J=16.12 Hz, 1H), 3-04-3.07 (m, 1H), 2.75-2.81 (m, 1H), 2.58 (d, J=13.2 Hz, 1H), 2.36 (s, 3H), 2.34 (s, 3H), 6.60-6.64 (m, 2H), 6.74-7.34 (m, 22H, Ar), 7.72 (s, 1H, NH); $^{13}$C NMR (CDCl$_3$, 100 MHz): δ/ppm 20.03, 20.98, 40.16, 46.29, 50.42, 53.19, 63.20, 65.73, 72.56, 98.58, 109.63, 123.91, 125.79, 126.32, 126.54, 126.89, 128.41, 128.64, 129.18, 129.32, 130.47, 131.55, 133.68, 136.09, 137.88, 138.03, 138.25, 138.41, 138.99, 139.09, 141.23, 177.96, 199.91. EI-MS: m/z 655 (M$^+$). Anal. Calcd for $C_{45}H_{41}N_3O_2$; C, 82.41; H, 6.30; N, 6.41; Found: C, 82.54; H, 6.42; N, 6.51.

5'-benzyl-4'-(4-tolyl)-5-spiro[3,2']oxindolopyrrolidino-4'-(4-methylphenyl)-1"-styryl-5-benzylidene-spiro[3'.3"]piperidi-4"-one (4i): Colorless crystals, 93%; $^1$H NMR (CDCl$_3$, 400 MHz): δ/ppm 4.96 (d, J=13.96 Hz, 1H), 4.71-4.75 (m, 1H), 4.35 (d, J=10.28 Hz, 1H), 3.79 (d, J=13.96 Hz, 1H), 3.67 (d, J=15.4 Hz, 1H), 3.35 (d, J=16.12 Hz, 1H), 3.03-3.06 (m, 1H), 2.76-2.78 (m, 1H), 2.60 (d, J=13.92 Hz, 1H), 2.36 (s, 3H), 2.34 (s, 3H), 6.60 (m, 2H), 6.64 (s, 1H), 6.84-7.35 (m, 21H, Ar), 7.64 (s, 1H, NH); $^{13}$C NMR (CDCl$_3$, 100 MHz): δ/ppm 21.20, 21.55, 39.40, 47.09, 53.03, 53.16, 61.22, 66.83, 71.12, 99.94, 109.19, 122.24, 124.06, 124.11, 126.33, 126.69, 127.96, 128.44, 128.60, 129.04, 129.19, 129.37, 129.41, 129.91, 130.12, 130.50, 131.87, 134.17, 136.81, 138.62, 138.76, 138.85, 139.14, 139.85, 141.02, 179.33, 197.84. EI-MS: m/z 655 (M$^+$). Anal. Calcd for $C_{45}H_{41}N_3O_2$; C, 82.41; H, 6.30; N, 6.41; Found: C, 82.53; H, 6.44; N, 6.52.

5'-benzyl-4'-(2-methoxyphenyl)-5-spiro[3,2']oxindolopyrrolidino-4'-(2-methoxyphenyl)-1"-styryl-5-benzylidene-spiro[3'.3"]piperidi-4"-one (4j): Colorless crystals, 85%; $^1$H NMR (CDCl$_3$, 400 MHz): δ/ppm 5.00-5.02 (m, 1H), 4.66 (d, J=13.96 Hz, 1H), 4.47 (d, J=10.28 Hz, 1H), 3.86 (s, 3H), 3.82-3.74 (m, 4H), 3.67 (d, J=16.12 Hz, 1H), 3.26 (d, J=13.96 Hz, 1H), 3.06-3.08 (m, 1H), 2.87-2.93 (m, 1H), 2.80 (d, J=13.92 Hz, 1H), 6.45 (m, J=13.92 Hz, 1H), 6.61 (d, J=8.08 Hz, 1H), 6.76-7.34 (m, 22H, Ar), 7.73 (s, 1H, NH); $^{13}$C NMR (CDCl$_3$, 100 MHz): δ/ppm 40.48, 46.40, 48.37, 52.25, 55.01, 55.45, 60.49, 65.14, 72.71, 97.48, 109.58, 110.71, 120.20, 120.81, 122.24, 123.55, 126.38, 126.43, 126.88, 127.79, 128.37, 128.56, 128.98, 129.12, 130.24, 130.92, 131.58, 134.11, 138.27, 139.26, 39.38, 139.47, 141.27, 179.92, 200.45. EI-MS: m/z 687 (M$^+$). Anal. Calcd for $C_{45}H_{41}N_3O_4$; C, 78.58; H, 6.01; N, 6.11; Found: C, 78.70; H, 6.13; N, 6.21, 40.48, 46.40, 48.37, 52.25, 55.01, 55.45, 60.49, 65.14, 72.71, 97.48.

5'-benzyl-4'-(3-methoxyphenyl)-5-spiro[3,2']oxindolopyrrolidino-4'-(3-methoxyphenyl)-1"-styryl-5-benzylidene-spiro[3'.3"]piperidi-4"-one (4k): Colorless crystals, 81%; $^1$H NMR (CDCl$_3$, 400 MHz): δ/ppm 5.01-5.04 (m, 1H), 4.68 (d, J=13.96 Hz, 1H), 4.49 (d, J=10.28 Hz, 1H), 3.84 (s, 3H), 3.80-3.82 (m, 1H), 3.79 (s, 3H), 3.65 (d, J=16.12 Hz, 1H), 3.28 (d, J=13.96 Hz, 1H), 3.05-3.07 (m, 1H), 2.86-2.92 (m, 1H), 2.82 (d, J=13.92 Hz, 1H), 6.44 (m, J=13.92 Hz, 1H), 6.62 (d, J=8.08 Hz, 1H), 6.77-7.38 (m, 22H, Ar), 7.71 (s, 1H, NH); $^{13}$C NMR (CDCl$_3$, 100 MHz): δ/ppm 40.45, 46.40, 48.39, 52.21, 55.09, 60.52, 65.17, 72.73, 97.50, 109.59, 110.74, 120.23, 120.78, 122.21, 123.50, 126.41, 126.39, 126.80, 127.80, 128.41, 128.61, 128.91, 129.14, 130.27, 130.93, 131.55, 134.12, 138.29, 139.30, 139.39, 139.46, 141.32, 179.89, 199.82. EI-MS: m/z 687 (M$^+$). Anal. Calcd for $C_{45}H_{41}N_3O_4$; C, 78.58; H, 6.01; N, 6.11; Found: C, 78.71; H, 6.12; N, 6.23.

5'-benzyl-4'-(4-methoxyphenyl)-5-spiro[3,2']oxindolopyrrolidino-4'-(4-methoxyphenyl)-1"-styryl-5-benzylidene-spiro[3'.3"]piperidi-4"-one (4l): Colorless crystals, 85%; $^1$H NMR (CDCl$_3$, 400 MHz): δ/ppm 4.99-5.02 (m, 1H), 4.66 (d, J=13.96 Hz, 1H), 4.46 (d, J=10.28 Hz, 1H), 3.83 (s, 3H), 3.80-3.82 (m, 1H), 3.79 (s, 3H), 3.64 (d, J=16.12 Hz, 1H), 3.29 (d, J=13.96 Hz, 1H), 3.04-3.08 (m, 1H), 2.87-2.93 (m, 1H), 2.83 (d, J=13.92 Hz, 1H), 6.46 (m, J=13.92 Hz, 1H), 6.61 (d, J=8.08 Hz, 1H), 6.78-7.39 (m, 22H, Ar), 7.73 (s, 1H, NH); $^{13}$C NMR (CDCl$_3$, 100 MHz): δ/ppm 40.42, 46.41, 48.40, 52.29, 55.11, 60.46, 65.22, 72.78, 97.80, 109.60, 110.76, 120.27, 120.79, 122.25, 123.52, 126.44, 126.41, 126.82, 127.86, 128.45, 128.64, 128.95, 129.17, 130.31, 130.95, 131.58, 134.16, 138.32, 139.36, 139.44, 139.49, 141.34, 179.85, 199.94. EI-MS: m/z 687 (M$^+$). Anal. Calcd for $C_{45}H_{41}N_3O_4$; C, 78.58; H, 6.01; N, 6.11; Found: C, 78.72; H, 6.11; N, 6.22.

5'-benzyl-4'-(3-nitrophenyl)-5-spiro[3,2']oxindolopyrrolidino-4'-(3-nitrophenyl)-1"-styryl-5-benzylidene-spiro[3'.3"]piperidi-4"-one (4m): Colorless crystals, 86%; $^1$H NMR (CDCl$_3$, 400 MHz): δ/ppm $^1$H NMR (CDCl$_3$, 400 MHz): δ/ppm 4.95 (d, J=14.68 Hz, 1H), 4.74-4.78 (m, 1H), 4.42 (d, J=10.28 Hz, 1H), 3.71-3.76 (m, 1H), 3.62 (d, J=16.12 Hz, 1H), 3.44-3.48 (m, 1H), 3.32 (d, J=16.16 Hz, 1H), 2.84-2.88 (m, 1H), 2.52 (d, J=13.2 Hz, 1H), 6.71 (d, J=8.08 Hz, 1H), 6.93-7.48 (m, 22H, Ar), 7.87 (s, 1H, NH); $^{13}$C NMR (CDCl$_3$, 100 MHz): δ/ppm 40.42, 46.91, 53.45, 53.54, 55.12, 61.28, 66.97, 71.18, 100.23, 109.28, 122.35, 124.11, 124.21, 126.40, 126.74, 127.29, 127.89, 128.51, 128.68, 128.69, 128.77, 129.29, 129.39, 130.32, 130.71, 134.66, 137.31, 138.67, 138.74, 138.78, 139.19, 141.11, 179.19, 197.81. EI-MS: m/z 717 (M$^+$). Anal. Calcd for $C_{43}H_{35}N_5O_6$: 71.95; H, 4.91; N, 9.76; Found: 71.87; H, 4.99; N, 9.88.

Figure 4:
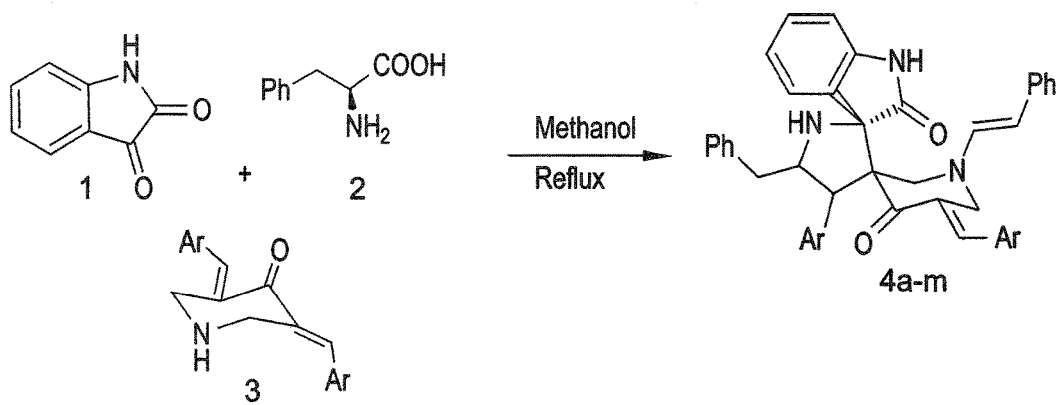
FIG. 4 shows the synthesis reaction of preparing N-arylidene piperidone tethered dispiropyrrolidines 4a-m.

Molecules possessing bis-arylidene piperidinone derivatives displayed excellent anti-cancer activity. It is believed that the good cytotoxic activity was due to the presence of bis-arylidene piperidinone structural motif. Inspired by these findings, the present inventors synthesized hybrid heterocycle comprising oxindole, pyrrolidine and the bis-arylidene piperidinone structural motifs. The methodology was based on the multicomponent dipolar cycloaddition reaction strategy outlined in FIG. 4, and involved a domino process comprising 1,3-dipolar cycloaddition reaction between (3E,5E)-3,5-bis(4-methylbenzylidene)piperidin-4-one and azomethine ylide 5 generated in situ from isatin 1 and L-phenylalanine 2 to afford spiroheterocycle 9 which subsequently reacts with 2-phenylacetaldehyde 8 generated in situ from azomethine ylide to afford the unusual N-substituted arylmethylidene piperidone tethered dispiropyrrolidine 4 through an enamine formation reaction. Optimization for this domino reaction was performed in different organic solvents. Initially the reaction was performed with an equimolar mixture of (3E,5E)-3,5-bis(4-methylbenzylidene) piperidin-4-one, isatin and L-phenylalanine in methanol. The reaction afforded the product only in 25% yield even after 10 hours under reflux. The starting precursor 3 was still present in the reaction mixture as evidenced by TLC. Later, the same reaction in 1:2:2.05 molar ratio was completed in 2 hrs (TLC) affording the product in good yield. The reaction was also performed under reflux in different solvents, viz., dioxane, dioxane/methanol (1:1 v/v) mixture, toluene, and acetonitrile. In all these reactions, the N-arylidene piperidone tethered dispiropyrrolidine 4 was formed only in moderate yields even after long reaction times. The best results were obtained only in heating the reaction mixture to reflux in methanol for 2 hours to afford the product as a single regioisomer in good yield. Consequently, all of the subsequent reactions were performed under this optimized reaction condition.

Figure 5:
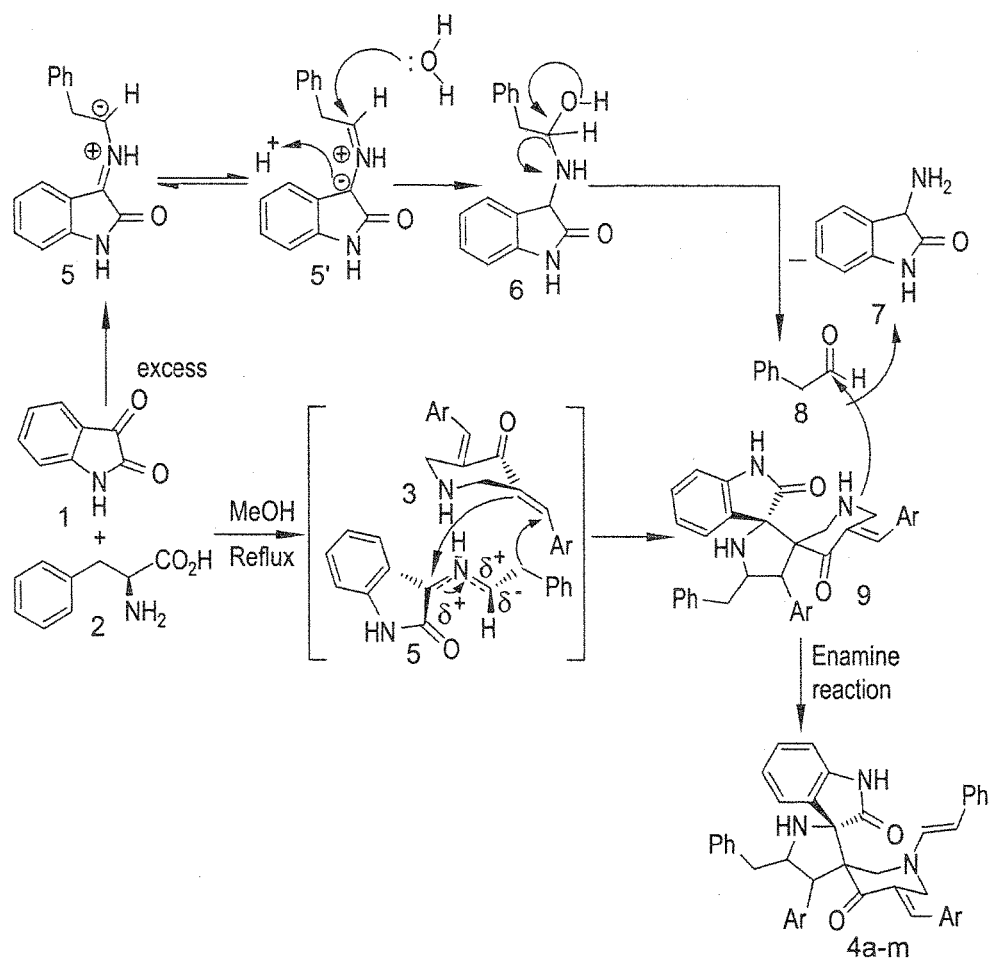
FIG. 5 shows the plausible mechanism for the regio- and stereo selective product formation through a domino sequence.

A feasible mechanism for the formation of unusual spirooxindolopyrrolidine tethered piperidinones through tandem transformation is illustrated in the reaction scheme of FIG. 5. Presumably, the reaction of istatin 1 L-phenylalanine 2 affords azomethine ylide 5 via decarboxylative condensation. This intermediate then adds regioselectively to one of the C=C bonds of 3 with the nucleophilic benzyl carbon of the azomethine ylide adding to the electron-deficient β-carbon of the azomethine ylide to form the cycloadduct 9.

The regiochemical outcome is also in accord with steric factors as well as possible secondary orbital interactions between the nitrogen lone pair and the carbonyl function during the cycloaddition favoring the formation of 9. Simultaneously, the azomethine ylide 5' was attacked by water molecule to furnish 2-phenylacetaldehyde 8 and 3-aminoindolin-2-one 7 as by product via compound 6. Subsequently, 2-phenylacetaldehyde was attacked by nitrogen lone pair of 9 to form 4 through enamine reaction.

A series of thirteen N-arylidene piperidone tethered dispiropyrrolidine 4 were synthesized. The structures of the newly synthesized spiro compounds (anti-cancer agents) were elucidated using spectroscopic studies. The various N-arylidene piperidinone tethered spiropyrrolidines (4a-m) are provided below in Table 1.

TABLE 1

Synthesis of Thirteen Spiropyrrolidines of Formula I

| Entry | Compounds | Ar | $IC_{50}$ value (48 hr) |
|---|---|---|---|
| 1 | 4a | phenyl | 19.00 |
| 2 | 4b | 2-bromophenyl | 49.00 |
| 3 | 4c | 4-bromophenyl | 24.00 |
| 4 | 4d | 2-chlorophenyl | 29.00 |
| 5 | 4e | 2,4-dichlorophenyl | 23.50 |
| 6 | 4f | 4-chlorophenyl | 36.00 |
| 7 | 4g | 2-methylphenyl | 22.00 |
| 8 | 4h | 3-methylphenyl | 31.00 |
| 9 | 4i | 4-methylphenyl | 37.00 |
| 10 | 4j | 2-methoxyphenyl | 39.00 |
| 11 | 4k | 3-methoxyphenyl | 41.00 |
| 12 | 4l | 4-methoxyphenyl | >50 |
| 13 | 4m | 3-nitrophenyl | >50 |

Figure 3:
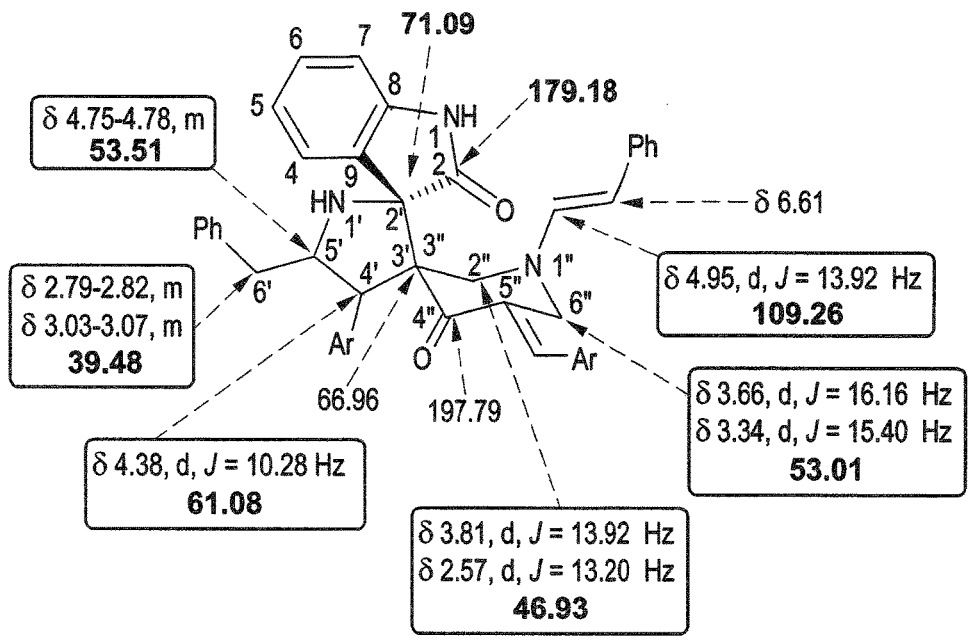

The spiropyrrolidines 4a-m were characterized by one and two dimensional NMR spectroscopic data as illustrated for 4a. The $^1$H NMR spectrum of 4a has a doublet at δ 4.38 ppm (J=10.28 Hz) for benzylic proton 4'-CH of the pyrrolidine ring. The multiplet at δ 4.75-4.78 ppm was assigned to 5'-CH based on its H, H-COSY correlation with 4'-CH. Further, the multiplets at δ 2.79-2.82 and 3.03-3.07 ppm were assigned to 6'-CH$_2$ as it shows H, H-COSY correlation with 5'-CH. From H, H-COSY correlations, the two doublets at δ 3.81 (J=13.92 Hz) and 2.57 ppm (J=13.20 Hz) can be assigned to 2"-CH$_2$ hydrogens, besides showing correlation with piperidinone carbonyl carbon at 197.79 ppm. The arylmethylidene proton 7"-CH appeared as a doublet at δ 4.95 ppm (J=13.92 Hz) while 8"-CH exhibited as a doublet at δ 6.61 ppm (J=15.00 Hz). The fact that the H-4' benzylic proton appeared as doublet at δ 4.38 ppm (J=10.28 Hz) clearly establishes the regiochemistry of the cycloaddition, as for the other possible regiomers that might have arisen from the cyloaddition, it should give a singlet. In the $^{13}$C NMR spectrum, the signals at 71.09 and 66.96 ppm were attributed to C-2' and C-3' carbons, respectively while the signals at 39.48, 46.93 and 53.01 ppm were assigned to the three methylene carbons (C-6', C-2" and C-6"). The signals at 179.18 and 197.79 were due to oxindole and piperidone carbonyl carbon, respectively (FIG. 3). The carbon chemical shifts of C-2", C-6', C-6", C-2', C-3', C-4' and C-5' were also confirmed from DEPT-135 spectroscopic analysis. Furthermore, the presence of molecular ion peak at m/z=627 (M$^+$) in the mass spectrum of 4a confirms the formation of spiroheterocyclic hybrid. The structure of other spiropyrolidines was also assigned by similar straight forward considerations. FIG. 3 shows the selected $^1$H and $^{13}$C chemical shifts of 4a.

Example 2

Cytotoxicity Assay

The synthesized series of compounds 4a-m stock solution were prepared by dissolved in DMSO (Sigma-Aldrich, St. Louis, Mo., USA) or dH$_2$O. The stock solutions were diluted with cell culture medium and used as a working solution. Different concentration of working solution was exposed to 5 to 7×10$^3$ cells seeded 96 well plates after 24 h incubation. DMSO/dH$_2$O was used as the solvent control. Nuclear morphological changes were monitored and photographed following treatment of synthesized compounds for 48 h using inverted microscope (Carl Zeiss, Jena, Germany). After incubation, plates were centrifuged and washed with cell culture medium. Subsequently, 20 μL of MTT solution [5 mg/mL in phosphate-buffered saline (PBS)] was added to each well, and the plates were protected from light and kept in CO$_2$ incubator at 37° C. for 4 h. The purple color formazan product was formed and dissolved in 100 μL of DMSO. The absorbance was monitored at 570 nm (measurement) and 630 nm (reference) using a 96 well plate reader (Bio-Rad, Hercules, Calif., USA). Data were collected for four replicates each and used to calculate the median effect dose or concentration, i.e., $IC_{50}$ using the Calcusyn software.

Figure 6:
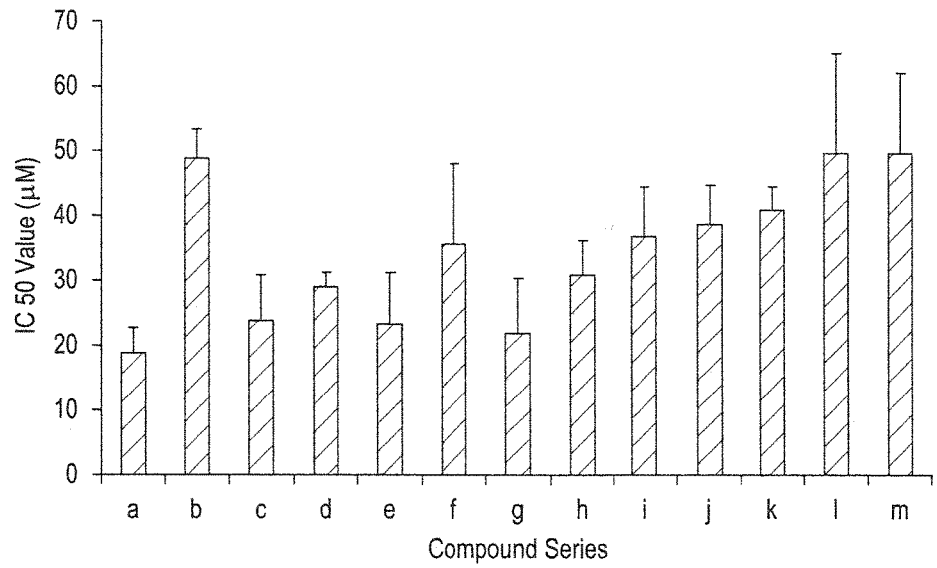
FIG. 6 is a graph showing the in vitro cytotoxicity analysis of synthesized compounds 4(a-m) against FaDu hypopharyngeal cancer cells for 48 hrs.
Figure 7:
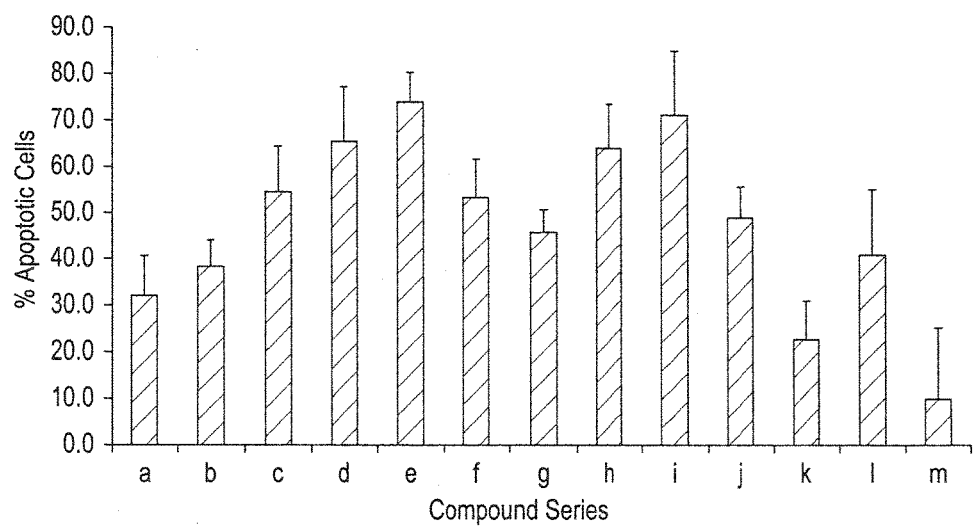
FIG. 7 is a graph showing the AO/EB dual staining data showing the response of FaDu hypopharyngeal cancer cells, in terms of apoptosis, to synthesized compounds 4(a-m) at 48 hr. The percentage of apoptotic cells is indicated by the histograms.

The cytotoxicity of synthesized compounds 4(a-m) on FaDu hypopharyngeal tumor cells was assessed for 48 h, in comparison with the commercial anti-cancer drug bleomycin under identical conditions (FIGS. 6&7). FIG. 6 displays the in vitro cytotoxicity analysis of synthesized compounds 4(a-m) against FaDu hypopharyngeal cancer cells for 48 hrs wherein the data are mean+SD of four replicates each. FIG. 7 shows the AO/EB dual staining data showing the response of FaDu hypopharyngeal cancer cells, in terms of apoptosis, to synthesized compounds 4(a-m) at 48 hr. The percentage of apoptotic cells is indicated by the histograms and the data shown are the means from triplicates. Vertical bars represent standard error of the mean. The synthesized compounds (4a-m) exhibit cytotoxicity in the order of (4a<4g<4e<4c<4d<4h<4f<4i<4j<4k<4b<4l<4m). Table 1 shows the $IC_{50}$ values of that synthesized series of compounds. The results suggested that compounds $IC_{50}$ values are slightly higher than the standard drug bleomycin ($IC_{50}$=21.8±7.3). Remarkably the compounds 4a and 4g bearing unsubstituted and 4-methyl moieties on aromatic rings exhibited an excellent cytotoxic property compared to rest of the compounds. Moreover, halogen and methyl substituted derivatives, viz., 4e with 2,4-dichloro, 4c with 4-bromo, 4d with 2-chloro and 4h with 3-methyl moiety on the phenyl rings showed good cytotoxicity against cancer cells. Among the derivatives with halogen substituents in the phenyl ring, compound 4e, and 4c showed good activity than other halogen derivatives. These cytotoxicity results revealed that with limited substituents on the aryl ring, it is difficult to discern the exact structure activity relationship with respect to electron withdrawing and donating group.

Example 3

Acridine Orange (AO) & Ethidium Bromide (EB) Fluorescent Probe for Assessing Cell Death Fluorescent microscopic analysis was carried out by acridine orange (AO) and ethidium bromide (EB) dual staining method. The synthesized compounds treated and untreated cancer cells were incubated with 10 μg/mL concentration of 1:1 acridine orange and ethidium bromide mixture of PBS solution, and observed under fluorescent microscope (Carl Zeiss, Jena, Germany) using a UV filter (450-490 nm). The viable and apoptotic or necrotic cells were counted from three hundred cells of each dose of the samples, and the respective percentages of apoptotic and necrotic cells were then calculated. The cells of interest were photographed. The data presented are representative of those obtained in at least three independent experiments conducted in triplicate.

Figure 8A:
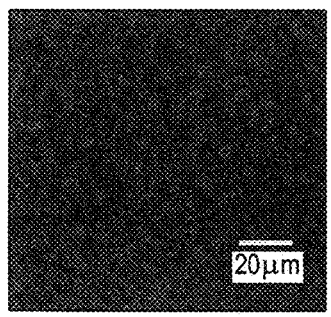
FIGS. 8A-8N shows the cytological features of compounds 4(a-m)-treated FaDu hypopharyngeal cancer cells (48 hours) at a magnification of 400×.
Figure 8B:
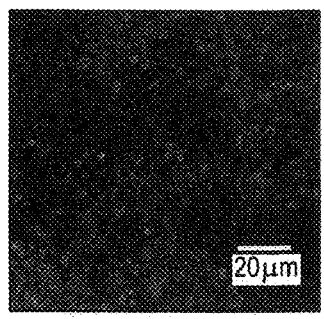
Figure 8C:
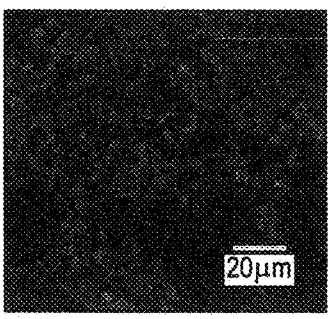
Figure 8D:
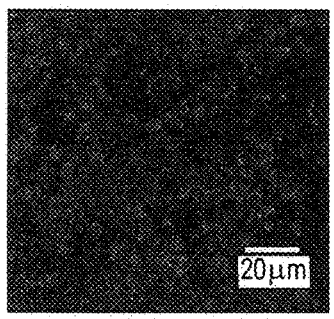
Figure 8E:
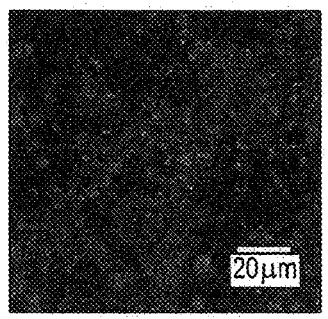
Figure 8F:
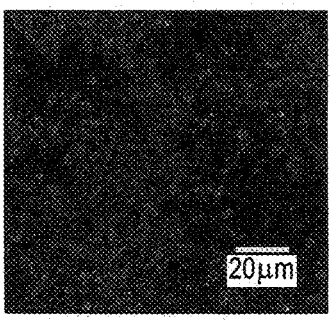
Figure 8G:
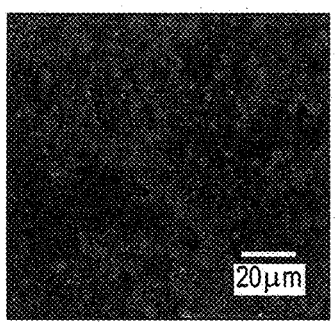
Figure 8H:
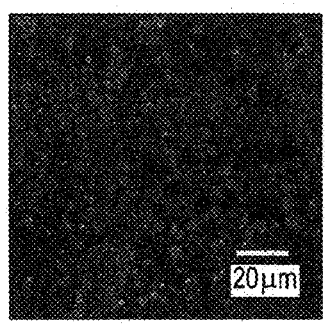
Figure 8I:
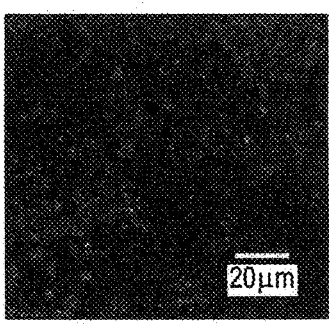
Figure 8J:
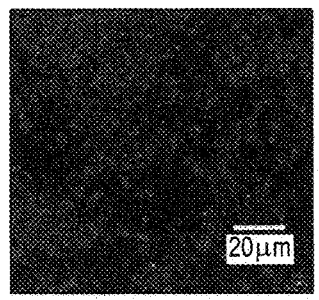
Figure 8K:
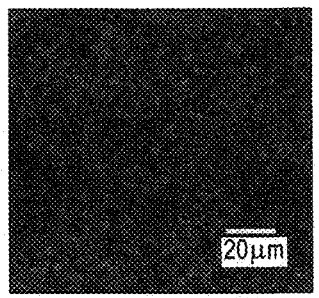
Figure 8L:
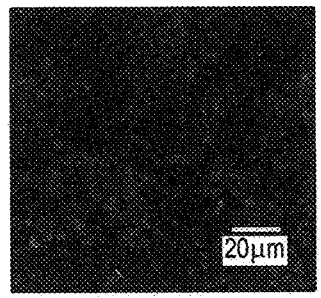
Figure 8M:
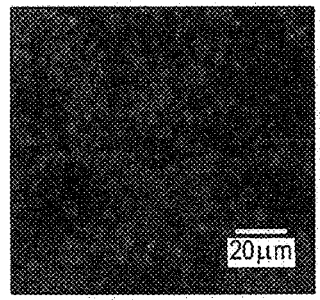
Figure 8N:
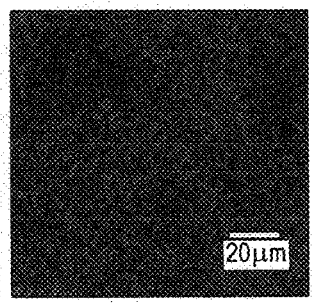

The quantification of apoptotic cell percentage was conducted as follows. The cytological morphology changes were analyzed in synthesized series of compounds treated cells. Acridine orange and ethidium bromide dual staining was performed, which indicated the cytoplasmic and nuclear morphological changes in the overall profile of the cell. After, the cancer cells were treated with $IC_{50}$ concentrations of synthesized compounds 4(a-m) for 48 h. The observations are classified into four types according to the cytoplasmic and nuclear morphology as follows: (i) viable cells are evenly green shining nuclei with a highly organized structure; (ii) early apoptotic cells are yellow-green shinning nuclei with crescent-shaped nuclear and condensed or fragmented chromatin (iii) late apoptotic cells are orange to red shining nuclei with chromatin condensation and fragmentation; and (iv) necrotic cells are evenly orange to red shining nuclei with increase the cell volume. Our present findings result suggested that synthesized compounds 4(a-m) induced apoptosis in FaDu cells, but less percentage of necrotic features are observed. Considering apoptosis in isolation, its incidence was the similar effects for all compounds. The data presented in FIG. 7 clearly show that the changes induced by the compounds 4(a-m) were consistent with the induction of both apoptotic cell death. Overall, the compounds under assay (4a<4g<4e<4c<4d<4h<4f<4i<4j<4k<4b<4l<4m) on FaDu cells indicated higher incidence of apoptosis for 48 hours in most of the cells with typical chromatin fragmented apoptotic cells as shown in FIGS. 8A-8N. These figures show cytological features of compounds 4(a-m)-treated FaDu hypopharyngeal cancer cells (48 hours) 400×. It was also indicated that the cells required short to longer incubation time for death only by apoptosis than necrosis. In other words, the early response was death by apoptosis, and the cells are not escaped succumbed to necrosis on short to prolonged treatment with the compounds 4(i-m).

It is to be understood that the present invention is not limited to the embodiments described above, but encompasses any and all embodiments within the scope of the following claims.

We claim:

1. An anti-cancer agent, comprising a dispiropyrrolidine tethered piperidone compound having the formula:

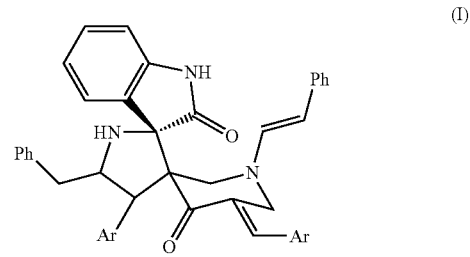

(I)

wherein Ph is a phenyl group and Ar is an aromatic group independently selected from the group consisting of phenyl, 2-bromophenyl, 4-bromophenyl, 2-chlorophenyl, 2,4, dichlorophenyl, 4-chlorophenyl, 2-methylphenyl, 3-methyl phenyl, 4-methylphenyl, 2 methoxyphenyl, 3-methoxyphenyl, 4-methoxyphenyl, and 3-nitrophenyl; or a pharmaceutically acceptable salt thereof.

2. A pharmaceutical composition, comprising the anti-cancer agent according to claim 1 and a pharmaceutically acceptable carrier, excipient or diluent.

3. A method for treating cancer, comprising the step of administering to a patient in need thereof a therapeutically effective amount of the anti-cancer agent for a cancer selected from the group consisting of colon, breast, prostate, and blood cancer according to claim 1.

4. The method for treating cancer according to claim 3, wherein the effective amount includes a dose amount that provides an in vivo concentration of about 10 μm to about 100 μm.

5. A method of making the anti-cancer agent of claim 1, comprising:
   providing a reaction mixture including indoline-2,3-dione, L-phenylalanine, and an N-arylidene piperidone derivative compound; and
   refluxing the reaction mixture in an organic solvent to yield the dispiropyrrolidine tethered piperidone of claim 1.

6. The method of making the anti-cancer agent according to claim 5, wherein a molar ratio of indoline-2, 3-dione:L-phenylalanine:N-arylidene piperidone derivative compound is 2:2:1.

7. The method of making the anti-cancer agent according to claim 5, wherein the reaction mixture is refluxed for about two hours.

8. The method of making the anti-cancer agent according to claim 5, wherein the organic solvent is methanol.

9. The method of making the anti-cancer agent according to claim 5, wherein the N-arylidene piperidone derivative compound includes (3E,5E)-3,5-bis(4-arylbenzylidene)piperidin-4-one.

* * * * *